United States Patent [19]

Chang et al.

[11] Patent Number: 4,748,328

[45] Date of Patent: May 31, 1988

[54] SINGLE PHOTON EMISSION COMPUTED TOMOGRAPH USING FOCUSED MODULAR COLLIMATORS

[75] Inventors: Wei Chang; Peter Kirchner; Karim Rezai, all of Iowa City, Iowa

[73] Assignee: The University of Iowa Research Foundation, Iowa City, Iowa

[21] Appl. No.: 884,080

[22] Filed: Jul. 10, 1986

[51] Int. Cl.⁴ .................. G01T 1/166; G21K 1/02
[52] U.S. Cl. .................. 250/363 R; 250/363 S; 250/505.1
[58] Field of Search ........ 250/505.1, 363 SB, 363 SC, 250/363 SG, 363 SH; 378/10

[56] References Cited

U.S. PATENT DOCUMENTS

| | | | |
|---|---|---|---|
| 4,079,257 | 3/1978 | Jatteau et al. | 250/252.1 |
| 4,389,569 | 6/1983 | Hattori et al. | 250/363 SB |
| 4,584,478 | 4/1986 | Genna et al. | 250/363 SB |

Primary Examiner—Carolyn E. Fields
Attorney, Agent, or Firm—Oblon, Fisher, Spivak, McClelland & Maier

[57] ABSTRACT

A single photon emission computed tomograph comprising a detector ring and a rotatable collimator assembly disposed within the detector ring. The rotatable collimator assembly comprises four collimator quadrants, and each of the four collimator quadrants comprises a plurality of collimator modules with their axes assembled in parallel. Each of the modules contains a plurality of inwardly directed channels focused to a single point on its own axis with a long focal length. The focal length of each of the collimator modules is individually and flexibly chosen to suit a particular imaging task. The four collimator quadrants are installed in the rotatable collimator assembly at a slightly different angular offset so as to achieve fine data sampling.

4 Claims, 3 Drawing Sheets

SINGLE PHOTON EMISSION COMPUTED TOMOGRAPH USING FOCUSED MODULAR COLLIMATORS

FIELD OF THE INVENTION

This invention relates generally to single photon emission computed tomographs (hereinafter referred to as "SPEC tomographs"). More particularly, it relates to a ring SPEC tomograph employing a plurality of focused collimator modules.

BACKGROUND OF THE INVENTION

In SPEC tomography, the patient's body is made to radiate photons, which of course radiate in all directions. To obtain useful information, it is necessary to select photons emitted in well-defined directions by a collimator and to measure the radiation intensity along each path with an appropriate detector. Then, by detecting photons from different directions along closely spaced paths and by using CT scan image reconstruction technology with appropriate modifications, the user can build up a "slice" image of the distribution of photon sources in the body.

The use of SPEC tomography to study brain function has received a strong impetus in the last few years primarily from the introduction of several new radio pharmaceutical tracers that can cross the blood brain barrier and localize in the brain parenchyma.

What is needed to take advantage of the availability of these new tracers is a cost effective high-performance SPEC tomography system. In order to have the resolution of such a system approach that of a positron emmission tomograph system (5-8 mm FWHM), a SPEC tomography system has to have a design optimized exclusively for brain SPEC tomography.

Most of the current SPEC tomographic approaches involve the use of a rotating detector system (scintillation camera or linear detector arrays) to collect information from multiple directions.

These approaches suffer from the problems that arise from complexity in electronic designs, the relative instability of PM tube gains with rotation, and very stringent uniformity requirements for detector response. These problems are analogous to those encountered in the design of the rotate-rotate type CT (third generation). It is well known that the rotate-stationary detectors was designed to avoid these problems. We believe that, for SPEC tomographic imaging, the ring type stationary detector arrangement offers the same advantages that have contributed to the improvements realized by fourth generation CT systems—namely, simplicity, stability, and tolerance to variation in detector responses. What is significant is the fact that most of the disadvantages inherent in fourth generation CT design do not appear to apply to SPEC tomographic systems utilizing stationary detectors. For example, the major criticism of the fourth generation CT design is that only a fraction of the detectors are utilized at any given time. In the stationary detector SPEC tomography design, nearly all of the detectors are in operation at all times during the imaging procedure.

To date, two groups have espoused this approach and have built stationary ring-type, discrete detector systems for SPEC tomographic imaging. Rogers, W. L.; Clinthrone, N. H.; Stamos, J.; et al., "SPRINT: A Stationary Detector Single Photon Ring Tomography for Brain Imaging," 1 *IEEE Trans. Med. Im.* p. 63 (1982); and Hirose, Y.; Ikeda, Y.; Higashi, Y.; et al., "A Hybrid Emmission CT Headtome II," 29 *IEEE Trans. Nucl. Sci. N.S.* p. 520 (1982). For each of these designs, the major component subject to circular rotation is the collimator.

Rogers et al achieve fan beam geometery in SPEC tomography data sampling by using slit apertures in a ring collimator. Data sampling by each detector consists of viewing a small strip (ray) of the target volume through one of the slit apertures. As the ring collimator indexes in rotation, the rays sampled sequentially by a particular detector form a fan. The resolution performance is excellant (8 mm FWHM at the center) and varies only slightly in different regions of the imaging plane. However, the low intrinsic efficiency of slit apertures and the limited number of slits on the ring make the collimator very insensitive. In addition, the slit collimator design discriminates against activity at depth and favors activity at close range. These characteristics indicate that the great majority of the detected photons are from the peripheral area of the target volume.

The approach disclosed by Hirose et al. uses a varying pitch collimator. Data sampling during rotation of the collimator also yields a fan beam pattern for each detector. The collimator was designed for high efficiency by today's standard. However, resolution at the center of the imaging field (11.5 mm FWHM) is too low to quality this design as belonging to the high resolution design category. Moreover, the technical problems involved in fabrication of this collimator make it difficult to extend its resolution performance beyond 10 mm FWHM at the center of the imaging field.

OBJECTS OF THE INVENTION

With a view of overcoming or ameliorating the shortcomings in each of the above-described existing approaches, it is an object of this invention to provide a circular ring detector SPEC tomographic system with a different type of rotating collimator, one specifically designed to achieve fine and precise fan beam data sampling with high performance characteristics.

SUMMARY OF THE INVENTION

Our new rotating collimator is composed of a plurality of focused collimator modules suitable for single multi-slice SPEC tomographic sampling. The collimator is in the form of a ring divided into four 90° sectors (or quadrants). Each quadrant is made up of a plurality of focused collimator modules arranged in parallel. Each focused collimator module has a array of channels each of which is a small tapered bore. All the channels in a module converge (or focus) to a focal point on the long axis of the module. This focal point has a long focal length. Behind the collimator modules is a stationary detector ring. When the collimator is rotated, each detector is collimated sequentially to different directions within a certain angular range.

BRIEF DESCRIPTION OF THE DRAWINGS

Various other objects, features, and attendant advantages of the present invention will be more fully appreciated as these become better understood from the following detailed descriptions and the accompanying drawings in which like reference characters designate like or corresponding parts throughout the several views and wherein.

DETAILED DESCRIPTION OF THE PRESENTLY PREFERRED EMBODIMENT

Figure 1:
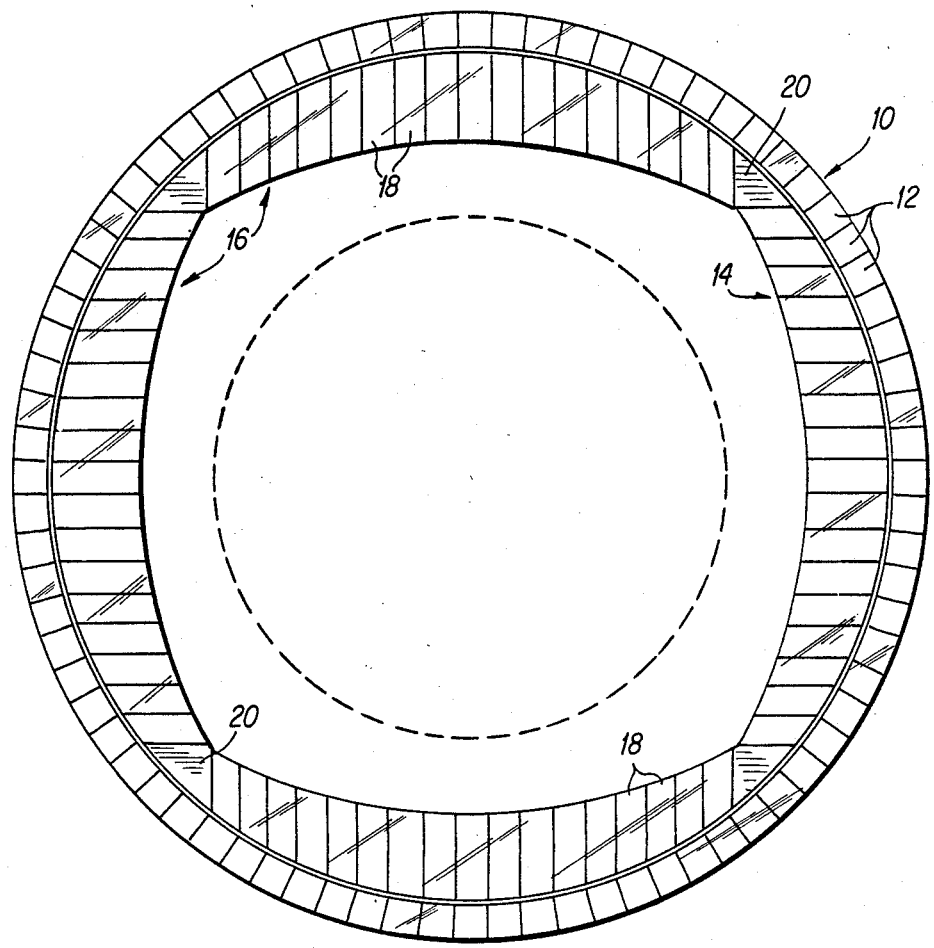
FIG. 1 shows the relationship between the detector ring and the collimator ring and its component modules.

Referring first to FIG. 1, a detector ring 10 consists of a plurality (N) of discrete NaI crystal detectors 12 with appropriate length and thickness, uniformly spaced over the whole 360° circle. Each detector 12 has its own PM tube assembly and light pipe, if necessary. A collimator ring assembly 14 consisting of collimator modules arranged in four quadrants 16 is concentric to and immediatly inside the detector ring 10.

Figure 2:
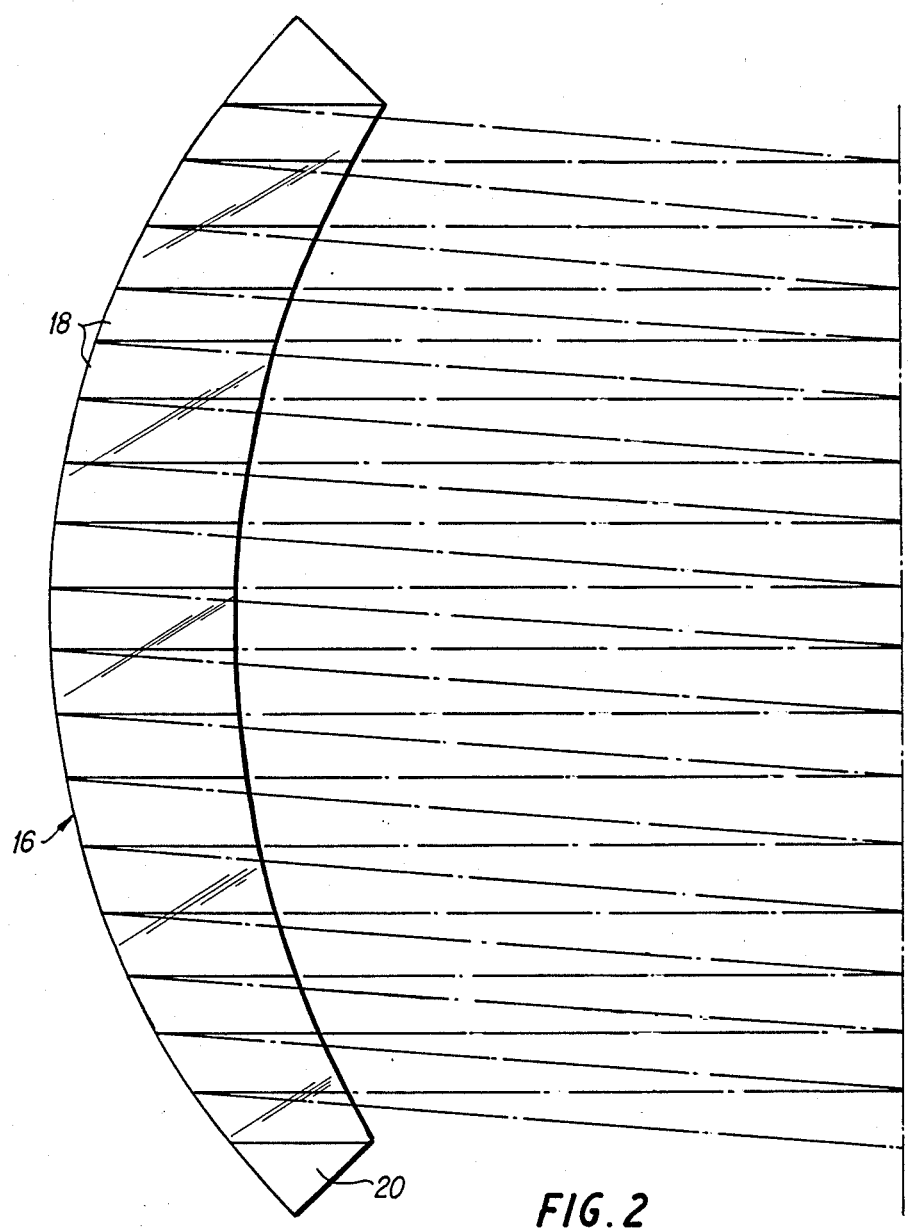
FIG. 2 shows a single quadrant of the collimator ring.
Figure 3:
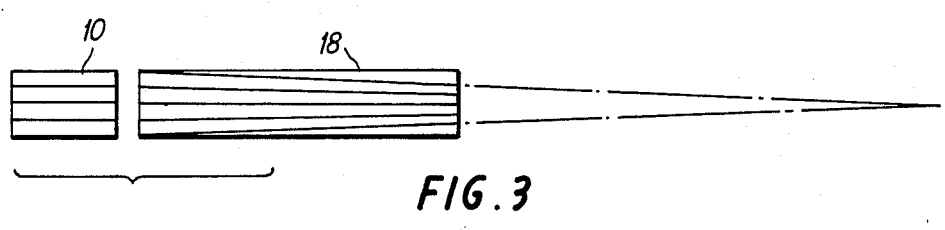
FIG. 3 shows a single cast collimator module.

Each quadrant of the ring collimator 16 is assembled from a plurality (M) of collimator modules 18, with the axes of the individual modules arranged in parallel. Each of the collimator modules 18 is a separate, small focused collimator unit. Each module is composed of multiple square channels 16 focused to a point along the long axes of the module with a long focal length. One arrangement is to have all the focal points of the modules in a quadrant lie on a straight line at some distance into the reconstruction volume, as shown in FIG. 2. Typically, each channel might be 3 to 4 cm long and 2 to 3 mm in width and height. The focusing effect of the collimator modules 18 contributes significantly to high performance in sensitivity and to resolution achieved deep inside the imaging volume. The data collected by each detector through a focused collimator module is associated with the direction of the axis of the module and is defined as a data path. Fan beam data sampling is formed by the discrete rotation of the ring collimator assembly 14 in steps of 360°/N degrees over a 90° range.

Each of the four quadrants 16 is basically identical to the other three, but each is installed in the collimator assembly 14 with its central axis tilted to a slightly different angle with respect to its radial direction. The purpose of the angular offsets is to achieve interlacing of the four fan beam data paths from the four quadrants 16 to achieve fine linear sampling in a total 360° rotation. The angular offsets are in the range of just greater than 0° to the angle subtended by each discrete crystal in the detector ring 10. Preferably the angular offset of each of the four quadrant ring collimators is in the range of 1.0° to 2.0°.

A lead wedge 20 is positioned between each pair of the adjacent collimator quadrants 16. The lead wedges 20 have the potential to house sample radioactive sources for calibrating those detectors which are temporarily blocked from "seeing" the target while the other detectors 12 are acquiring data. Thus, the response of each detector 12 can also be monitored while imaging procedure is in progress.

A proven CT technique that is utilized as a key feature of this design is the "quarter ray offset" arrangement of the sampled rays. See, e.g., Joseph, P. M., "Artifact in Computed Tomography" in *Technical Aspects of Computed Tomography*, Newton, T. H., and Potts, D. G. (editors), C. V. Mosby Co. (St. Louis, Mo., 1981). This is accomplished by critical adjustment of the offset angle of each quadrant collimator 16. This arrangement effectively increases linear sampling rate by about a factor of two. It is the increased linear sampling that allows the high resolution performance to be realizable deep inside the imaging field.

Preferably, each of the four collimator quadrants is installed at a second angular offset on the order of ¼ of the first angular offset, discussed above, to achieve the "quarter ray offset."

Figure 4:
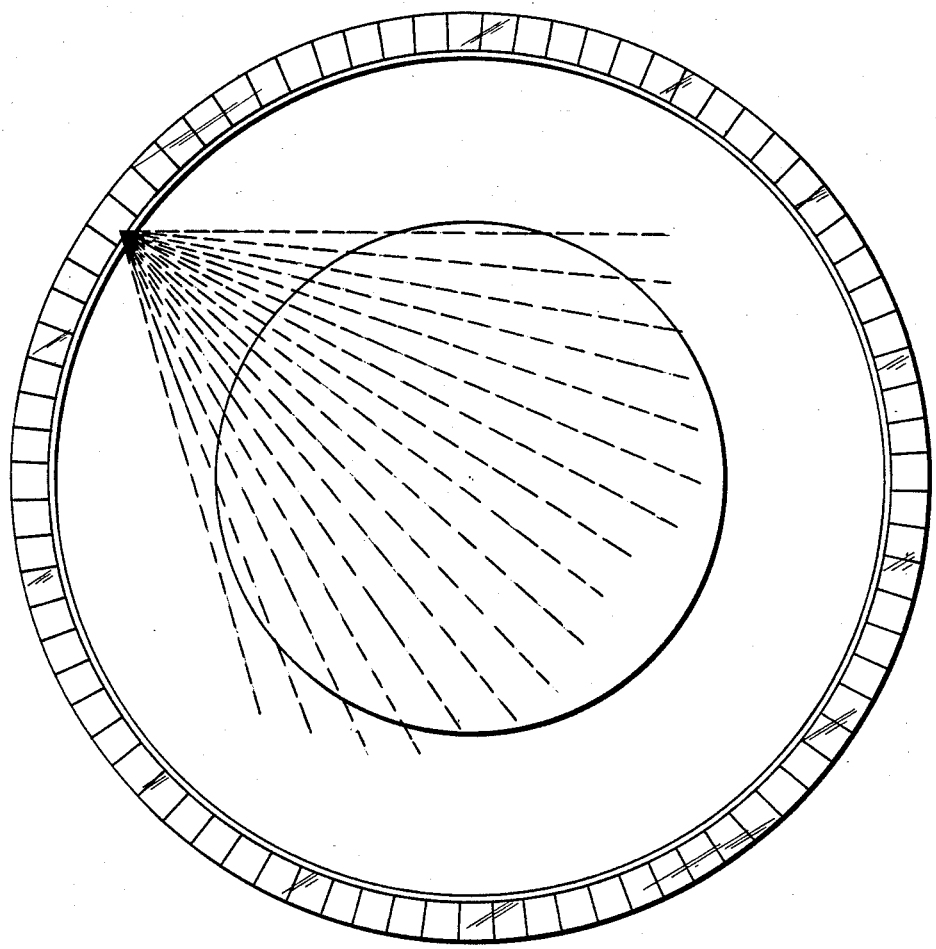
FIG. 4 is a schematic illustration showing the fan beam data paths sequentially acquired by a detector as the collimator assembly rotates through 90°.

As shown in FIG. 4, one-fourth of the overall fan beam data sampling is accomplished after the rotation of the collimator assembly through 90°. Three more sets of similar fan beam data fill in the gaps between the sampled rays after a full 360° rotation. Each view is defined by each individual detector fan, which consists of 4×M data paths after completion. Image reconstruction is carried out by fan beam reconstruction algorithms similar to those used in CT, except for modifications appropriate for SPEC tomographic reconstruction.

Collimators can be designed to achieve 7 to 10 mm tomographic resolution FWHM at the center of the imaging fields. The tomographic resolution at the periphery of the imaging field should be very close to the resolution at the center and will depend on collimator module design. Such performance characteristics indicate that the system disclosed here represent the highest resolution SPEC tomographic system conceived to date. At the same time, the sensitivity per slice also should be adequate for clincal imaging of the new I-123 and Tc-99m brain agents. We predict that the sensitivity of this system for a 20 cm diameter phantom containing Tc-99m will be about 3000 cps/uci/cc, which is about three times the sensitivity provided by the best current design for the same 8 mm resolutions and 10 mm slice thickness. The possibility that detectors can be arranged on a circle of relatively small radius (17 cm) also contributes to the system's high sensitivity.

Another important aspect of the subject collimator design is its practicality from the point of view of manufacturing. Although the M modules 18 in each quadrant 16 at first glance appear different in size and in length, they are actually different sections of a longer focused collimator. Therefore, only one mold is needed for the casting process. This approach not only reduces manufacturing cost, but also assures that all of the modules will be nearly identical in quality. If an error should occur in the manufacturing of the collimator (e.g., in the angulation of the channels with respect to the collimator module), it will be present to the same extent in every module. Therefore, the error can be remedied in the assembly stange or its effects compensated via software in the image reconstruction stage.

Collimator casting technology of the type employed in this sytem is available commercially. Chang, W.; Bruch, P.; Wesolowski, C.; et al., "Performance of Cast Collimator For SPECT Imaging," 26 *J. Nucl. Med.* p. 44 (1985). Thus, the casting technology does not constitute a part of this invention.

The single slice scanner described is just the first step in demonstrating the focused modular collimator approach to brain SPECT tomography. The same basic collimator design can be applied to build a multi-slice collimator which provides SPEC tomographic data with appropriate multi-slice stationary detector designs. Moreover, the detector ring described here is not limited to ring detectors employing a large number of discrete detectors. A one piece cylindrical detector with a position sensitive network can also be used with the disclosed collimator design. Logan, K. W.; and Holmes, R. A., "Missouri University MultiPlane Imager (MUMPI): A high Sensitivity Rapid Dynamic ECT Brain Imager," 25 *J. Nucl. Med.* p. 105 (1984); and Clinthorne, N. H.; Rogers, W. L.; Koral, K. F.; et al., "A Modular Detector for SPECT," 26 *J. Nucl. Med.* p. 11 (1985).

When multiple discrete detectors are used to form a detector ring, the detector ring should have the option (in certain situations) to rotate a few degrees with respect to its isocenter to increase the number of data sampling directions from the limited number of detectors.

What is claimed as new and desired to be secured by letters patent of the United States is:

1. A single photon emission computed tomograph comprising:
   (a) a detector ring and
   (b) a rotatable collimator assembly disposed within said detector ring, said rotatable collimator assembly comprising four collimator quadrants, each of said four collimator quadrants comprising a plurality of collimator modules with their axes assembled in parallel, each of said modules containing a plurality of inwardly directed channels focused to a single point on its own axis, the focal length of each of said collimator modules being individually chosen to suit a particular imaging task,
   (c) wherein each of said four collimator quardants is installed in said rotatable collimator assembly at a slightly different first angular offset to achieve fine data sampling, the first angular offsets being in the range of just greater than 0° to the angle subtended by each discrete crystal in said detector ring.

2. A single photon emission computed tomograph as recited in claim 1 wherein said first angular offset of each of said four quadrant ring collimators is in the range of 1.0° to 2.0°.

3. A single photon emission computed tomograph as recited in claim 1 wherein each of said four collimator quadrants is installed at a second angular offset on the order of ¼ of said first angular offset to achieve quarter ray offset in data sampling.

4. A single photon emission computed tomograph as recited in claim 1 and further comprising a lead wedge disposed between each two adjacent ones of said collimator quadrants.

* * * * *